United States Patent
Toepfer et al.

(10) Patent No.: US 7,803,317 B2
(45) Date of Patent: Sep. 28, 2010

(54) METHOD FOR DECONTAMINATING TEMPERATURE-SENSITIVE OBJECTS

(75) Inventors: Hans-Joachim Toepfer, Backnang (DE); Markus Kostron, Remseck (DE)

(73) Assignee: Kaercher Futuretech GmbH, Winnenden (DE)

( * ) Notice: Subject to any disclaimer, the term of this patent is extended or adjusted under 35 U.S.C. 154(b) by 9 days.

(21) Appl. No.: 11/818,173

(22) Filed: Jun. 12, 2007

(65) Prior Publication Data

US 2009/0169426 A9    Jul. 2, 2009

Related U.S. Application Data

(63) Continuation of application No. PCT/DE2005/002240, filed on Dec. 13, 2005.

(30) Foreign Application Priority Data

Dec. 13, 2004   (DE) ................. 10 2004 062 368

(51) Int. Cl.
*A61L 2/20* (2006.01)
*A61L 2/04* (2006.01)

(52) U.S. Cl. .......................... 422/33; 422/28
(58) Field of Classification Search ............ 422/28, 422/33
See application file for complete search history.

(56) References Cited

U.S. PATENT DOCUMENTS

| | | | |
|---|---|---|---|
| 3,489,505 A | * | 1/1970 | Sonnenschein et al. ..... 422/116 |
| 5,008,079 A | | 4/1991 | Wutzler et al. |
| 5,122,344 A | | 6/1992 | Schmoegner |
| 5,700,426 A | * | 12/1997 | Schmitthaeusler et al. .... 422/29 |

FOREIGN PATENT DOCUMENTS

| | | |
|---|---|---|
| DE | 1 738 709 | 1/1957 |
| DE | 29 21 915 | 12/1980 |
| DE | 34 13 743 A1 | 10/1985 |
| DE | 34 29 346 A1 | 2/1986 |
| DE | 36 25 847 A1 | 2/1988 |
| DE | 38 42 285 A1 | 7/1989 |
| DE | 38 35 857 A1 | 4/1990 |
| DE | 198 23 163 A1 | 5/1999 |
| DE | 698 21 825 T2 | 12/2004 |
| EP | 0 109 352 | 5/1984 |
| EP | 0 880 972 A2 | 12/1998 |
| GB | 2 055 289 A | 3/1981 |
| WO | WO 03/035118 A2 | 5/2003 |

OTHER PUBLICATIONS

Vortwort zue Liste der vom Robert Koch-Institut geprueften und anerkannten Desinfektionsmittel und -verfahren; Jan. 2003; pp. 72-95.

* cited by examiner

*Primary Examiner*—Sean E Conley
(74) *Attorney, Agent, or Firm*—Harness, Dickey & Pierce, P.L.C.

(57) ABSTRACT

An apparatus for decontamination of objects, such as temperature-sensitive devices for military applications, comprises a vacuum chamber having an internal space for receiving an object to be decontaminated. A vacuum pump produces a vacuum in the internal space. A heater is used for heating the internal space. A first arrangement is provided for ventilation of the internal space, and a second arrangement is provided for filling the internal space with a gaseous chemical decontamination agent. The apparatus can be used optionally for disinfection or detoxification, with a low decontamination temperature being sufficient in both cases because of the low pressure in the chamber.

12 Claims, 1 Drawing Sheet

METHOD FOR DECONTAMINATING TEMPERATURE-SENSITIVE OBJECTS

CROSS REFERENCES TO RELATED APPLICATIONS

This application is a continuation of International Patent Application No. PCT/DE2005/002240, filed on Dec. 13, 2005 designating the U.S., which international patent application has been published in German language as WO 2006/063569 A2 and claims priority from German patent application DE 10 2004 062 368.6, filed on Dec. 13, 2004. The entire contents of these priority applications are incorporated herein by reference.

BACKGROUND

The present invention relates to an apparatus and a method for decontamination of objects, in particular for detoxification or disinfection of small, temperature-sensitive military devices.

In terms of the present invention, decontamination means specific eradication/removal of radioactive substances and/or specifically rendering safe or removing biological or chemical substances which, without such measures, would represent a hazard to the health or even to the life of personnel. Such substances may be the result of the use of NBC agents for military or terrorist purposes. Furthermore, the substances may also lead to contamination of personnel or object as a result of accidents. Decontamination measures include nuclear radiation eradication (N decontamination), disinfection (B decontamination) and detoxification (C decontamination), with different decontamination agents and procedures being used depending on the nature of the decontamination. The present invention relates in particular to the detoxification and disinfection of small temperature-sensitive appliances, for example of telescopic sights or other optical or electronic components.

German patent application DE 34 29 346 A1 discloses a decontamination method in which a mixture of hot air and steam is used as decontamination agent. Any other heated gas instead of hot air may allegedly be used. In particular, the use of exhaust gases from combustion processes is proposed. An important factor for the success of this known method is the high temperatures of, for example, 170° C. This known method is therefore not suitable for decontamination of temperature-sensitive objects. Furthermore, the known method does not ensure reliable disinfection in the case of critical biological agents, such as mycotoxins or anthrax spores.

The method known from DE 34 29 346 A1 differs from another known method, which is mentioned in the introductory portion of the specification in DE 34 29 346 A1, by the use of a hot-air/hot-gas-vapor mixture at ambient pressure. In the case of the latter, the decontamination is carried out solely by means of hot vapor at a maximum pressure of 4 bar. The decontaminated objects are dried with hot air in a phase that follows. However, this known method also does not ensure adequate disinfection of critical biological agents, and, furthermore, it is not suitable for detoxification of temperature-sensitive objects.

DE 36 25 847 A1 discloses a decontamination chamber which is intended in particular for decontamination of items of clothing. In this case as well, a hot-gas/vapor mixture is used as the decontamination agent, using flue gases or exhaust gases from combustion processes. In the case of this known decontamination chamber, the decontamination process is once again carried out at high temperatures and at ambient pressure.

DE 34 13 743 A1 and DE 38 35 857 A1 both disclose apparatuses for the production of hot vapor for decontamination of items of clothing and equipment. The use of hot vapor and, in addition to this, the use of combustion exhaust gases as a decontamination agent also makes these known apparatuses unsuitable for the decontamination of temperature-sensitive items of equipment, however. Furthermore, these known methods also do not ensure adequate decontamination of critical biological agents.

Various methods for disinfection of objects are known from the so-called RKI list, which is issued by the Robert-Koch Institute in Germany and is published in the Federal Health Gazette ("Bundesgesundheitsblatt") of the Federal Republic of Germany No. 1-2003. A distinction is made between thermal methods and chemical methods. The former generally make use of hot vapor for disinfection, with the objects to be disinfected being accommodated in a chamber which is repeatedly evacuated and into which vapor pulses are then introduced. Methods are mentioned which operate with a vapor temperature of 75° C., which is a relatively low temperature in comparison to the decontamination methods described above. The chemical disinfection methods are based primarily on the use of chemical disinfection agents, such as formaldehyde, peracetic acid or chlorine. The RKI list also mentions chemo-thermal disinfection washing methods in which washing is carried out using chemical disinfection and cleaning agents at temperatures from 60° C. to 70° C.

DE 29 21 915 A1 describes an apparatus and a method for sterilization of thermally unstable materials in the medical field. The goal is to satisfactorily sterilize objects with narrow tubes or flexible tubes, such as endoscopes or catheters. Since small condensation droplets can block the pores and capillaries of such objects and can then absorb a disinfection agent in the form of vapor, the sterilization chamber is first of all repeatedly and alternately purged with an agent gas, and is ventilated again. By way of example, the sterilization chamber is first filled with water-aldehyde vapor at a reduced pressure of, for example 6 kPa. The chamber is filled to a pressure which is below the saturation pressure, for example to 16 kPa. The air-aldehyde-vapor mixture is then sucked off again down to a value of, for example 6 kPa. This process is repeated several times until it can be assumed that even very small cavities in the object to be sterilized have been filled with the agent gas. The operating pressure in the sterilization chamber is then raised above the saturation value of the agent, and is kept constant throughout a time during which it acts. The actual sterilization process is therefore carried out at a pressure which is above the saturation pressure, so that the agent is partially in condensed form.

SUMMARY

It is an object to provide a method and an apparatus by means of which temperature and/or water sensitive items of equipment, such as optical or electronic appliances, can be easily and reliably decontaminated. It is particularly an object to provide a method and an apparatus for detoxification or disinfection of temperature-sensitive and/or water-sensitive items of equipment. It is another object to provide a simple and robust method and apparatus for decontamination of sensitive devices in military operational conditions.

In view of the above, there is provided an apparatus for decontamination of temperature-sensitive objects, the apparatus comprising a vacuum chamber having internal walls surrounding an internal space for receiving an object to be decontaminated, comprising a vacuum pump for generating a vacuum in the internal space, the vacuum pump being configured to evacuate the internal space to an internal pressure of less than 50 Pa, comprising a heater for heating the internal space, the heater comprising at least one heat radiator arranged in the internal space and a casing heater designed to heat the internal walls, comprising a first arrangement for ventilating the internal space, comprising a second arrangement for filling the internal space with a gaseous chemical decontamination agent, the second arrangement comprising a reservoir for chemical decontamination agents and a supply line connecting the reservoir to the internal space, such that the chemical decontamination agent reaches the internal space in gaseous form, comprising a pressure gauge for determining an internal pressure in the internal space, and comprising a control unit designed for controlling the second arrangement as a function of the internal pressure.

There is also provided a method for removing biological contaminants from an object, comprising the steps of: providing a vacuum chamber having inner walls surrounding an internal space, inserting the object into the internal space, evacuating the internal space by means of a vacuum pump to an internal pressure of less than 50 Pa, heating the internal space by means of a heater, and supplying a gaseous chemical decontamination agent into the internal space, and ventilating the internal space subsequently, wherein the internal space is heated by means of at least one heat radiator arranged in the internal space, and by means of a casing heater designed to heat the internal walls, wherein a pressure rise in the internal space is determined while the internal space is being filled with the gaseous chemical decontamination agent, and wherein the gaseous chemical decontamination agent is supplied as a function of the pressure rise.

The new apparatus and method are based on a number of ideas. On the one hand, an apparatus is provided by means of which temperature-sensitive objects can optionally be detoxified and/or disinfected. Detoxification can be carried out by evacuating the internal space of the vacuum chamber, preferably down to about 1 Pa (virtually complete vacuum). Additionally, the internal space is heated, preferably to a temperature of about 75° C. In normal pressure conditions (ambient pressure), this temperature would be too low to allow the chemical contamination to vaporize. However, the reduced pressure in the chamber considerably reduces the boiling point of all known substances. In other words, the reduced pressure ensures that chemical contaminants are vaporized even at the relatively low maximum temperature of about 75° C. The vaporized contaminants are removed from the internal space of the chamber by the subsequent ventilation process. If required, the process of evacuation, heating and ventilation can be repeated several times. This allows temperature-sensitive objects to be reliably detoxified, even without use of hot vapor, that is to say by pure vaporization of the contaminating substances.

Alternatively or in addition, a chemical decontamination agent can be used and/or the objects to be decontaminated can be irradiated with UV light, in order to produce free radicals which react with the substances to be decontaminated. Preferably, the chamber is filled with a gaseous, chemical decontamination agent. The novel apparatus therefore also offers the capability to reliably detoxify objects, likewise at desired low temperatures.

The new apparatus and method are based on the idea of detoxification (C decontamination) and disinfection (B decontamination) at very low pressures, ideally in a vacuum. This allows a precisely defined atmosphere to be produced in the chamber, which ensures reliable decontamination of the objects located in the chamber as a function of the decontamination agents used and as a function of the selected temperature. Since the chamber allows both B decontamination (disinfection) and C decontamination (detoxification), it can be used very flexibly. The novel apparatus therefore makes it possible to reduce the decontamination appliances and systems required for military purposes.

Carrying out the decontamination at low pressures and preferably in a vacuum allows to reduce the decontamination temperatures without adversely affecting the success of the decontamination process. The novel method and apparatus can therefore be used successfully for B or C decontamination of temperature-sensitive objects, in particular including those which cannot be decontaminated using reactive chemicals in wet-chemical processes.

The heater comprises at least one heat radiator, in particular an infrared radiator, which is or are arranged in the internal space, as well as a casing heater, which is designed to heat internal walls of the vacuum chamber. The casing heater is preferably in the form of an electrical casing heater.

Heat radiators have the advantage that the objects to be decontaminated can be reliably heated to the desired decontamination temperature even in a vacuum. This is of high importance, since the objects cool down during evacuation of the chamber. On the other hand, it has been found that a casing heater can heat the objects in the chamber only with enormous difficulty, if at all, since there is no heat transfer medium in a virtually complete vacuum. In other words, the use of heat radiators contributes to ensuring that the objects reach the temperatures required for successful decontamination. The casing heater has the advantage that it prevents condensation of decontamination agent on the inner walls of the chamber. This ensures that no decontamination agent is "withdrawn" from the decontamination process. Only the combination of the two heating methods reliably allows decontamination in all operational conditions.

A pressure gauge is provided for determination of the internal pressure in the internal space, as well as a control unit which is designed to control the second arrangement as a function of the internal pressure. From the process point of view, a pressure rise in the internal space is determined while the internal space is being filled with the gaseous chemical decontamination agent, and the gaseous chemical decontamination agent is supplied as a function of the pressure rise.

These features are particularly advantageous for decontamination of objects at a very low pressure or in a vacuum. In this case, the pressure gauge can be used to very easily and reliably determine the concentration of the decontamination agent in the chamber without any need to provide specific gas sensors in the chamber for this purpose. Furthermore, the setting and/or monitoring of the decontamination agent concentration by means of the internal pressure in the chamber is also highly advantageous because there are only a relatively small number of gas molecules in the chamber at the low operating pressures which are used according to the present invention, so that a concentration measurement by means of a gas sensor has a high level of statistical errors superimposed on it.

In a refinement, the at least one heat radiator and the casing heater can be controlled independently of one another. This refinement has the advantage that the heating power can be optimally controlled throughout the course of the decontamination process.

In a further refinement, the casing heater is designed to heat all of the internal walls of the vacuum chamber. In other words, in this refinement, the vacuum chamber is heated on all sides, including the door areas. This makes it possible to optimally prevent "loss of agent" resulting from condensation being formed.

In a further refinement, the heater is designed such that it can heat the internal space up to 200° C.

During decontamination of temperature-sensitive objects, the heating power is limited such that the internal space and the objects located therein do not become any hotter than about 75° C. Experiments by the applicant have shown that this temperature range is on the one hand sufficiently low not to damage optical and/or electronic components and appliances such as those which are required in particular for military purposes, during the decontamination process. On the other hand, this temperature range in conjunction with the low pressures which can be set by means of the vacuum chamber ensures reliable detoxification and disinfection. On the other hand, a heater according to this preferred refinement widens the field of application of the apparatus, and this is a major advantage for military operational purposes.

In a further refinement, the novel apparatus and the novel method comprise at least one UV radiator, which is arranged in the internal space in order to irradiate the objects.

The additional provision of at least one UV radiator widens the field of application of the novel apparatus particularly for disinfection. The flexibility and the operational range are thus further increased.

In a further refinement, the second arrangement comprises a vaporizer for condensation-free vaporization of a decontamination agent provided in the reservoir.

This refinement increases the field of application of the novel apparatus and of the novel method even further. In particular, this makes it easier to use decontamination agents which are liquid or solid (preferably in the form of tablets) at room temperature and in ambient conditions. At the same time, condensation-free vaporization ensures that the decontamination agents completely fill the internal space of the chamber with the intended concentration and thus reliably reach all the accessible points of an object to be decontaminated.

In a further refinement, the supply line can be heated completely.

This refinement even more reliably suppresses the condensation of a vaporized decontamination agent when it is introduced into the chamber. The process parameters for decontamination can therefore be ensured even more reliably. In consequence, this also results in even more reliable decontamination success.

It is particularly preferable for the pressure gauge to be designed to detect a pressure difference of at least 1 Pa.

A pressure gauge such as this makes it possible to determine the decontamination agent concentration particularly accurately since even minor pressure differences can be detected accurately. The accurate determination of the concentration of the decontamination agent in the chamber allows the decontamination agent to be supplied in an economic form, which means that the major reduction in pressure can also be largely maintained during the decontamination process. This allows the entire decontamination process to be carried out more effectively and reliably.

From the process point of view, it is also preferable for the decontamination agent to define a saturation pressure, and for the internal pressure in the internal space to be kept below the saturation pressure all the time.

In this case, the decontamination agent concentration determined by means of the pressure rise corresponds very accurately to the concentration that is actually present in the chamber. Maintenance of the process parameters can accordingly be ensured even more accurately and reliably.

In a further refinement, the second arrangement is designed such that it fills the internal space with the gaseous decontamination agent by means of a reduced pressure.

As an alternative to this, it is basically possible to blow the gaseous decontamination agent into the internal space of the chamber by means of a pump or the like. The preferred refinement is simpler, since a pump is provided in any case in order to produce a reduced pressure in the chamber. Furthermore, because of the reduced number of parts, the preferred refinement can also be implemented more easily and can be physically smaller, thus in particular advantageously assisting mobility.

It goes without saying that the features mentioned above and those which are still to be explained in the following text can be used not only in the respectively stated combination but also in other combinations or on their own without departing from the scope of the present invention.

DESCRIPTION OF PREFERRED EMBODIMENTS

Figure 1:
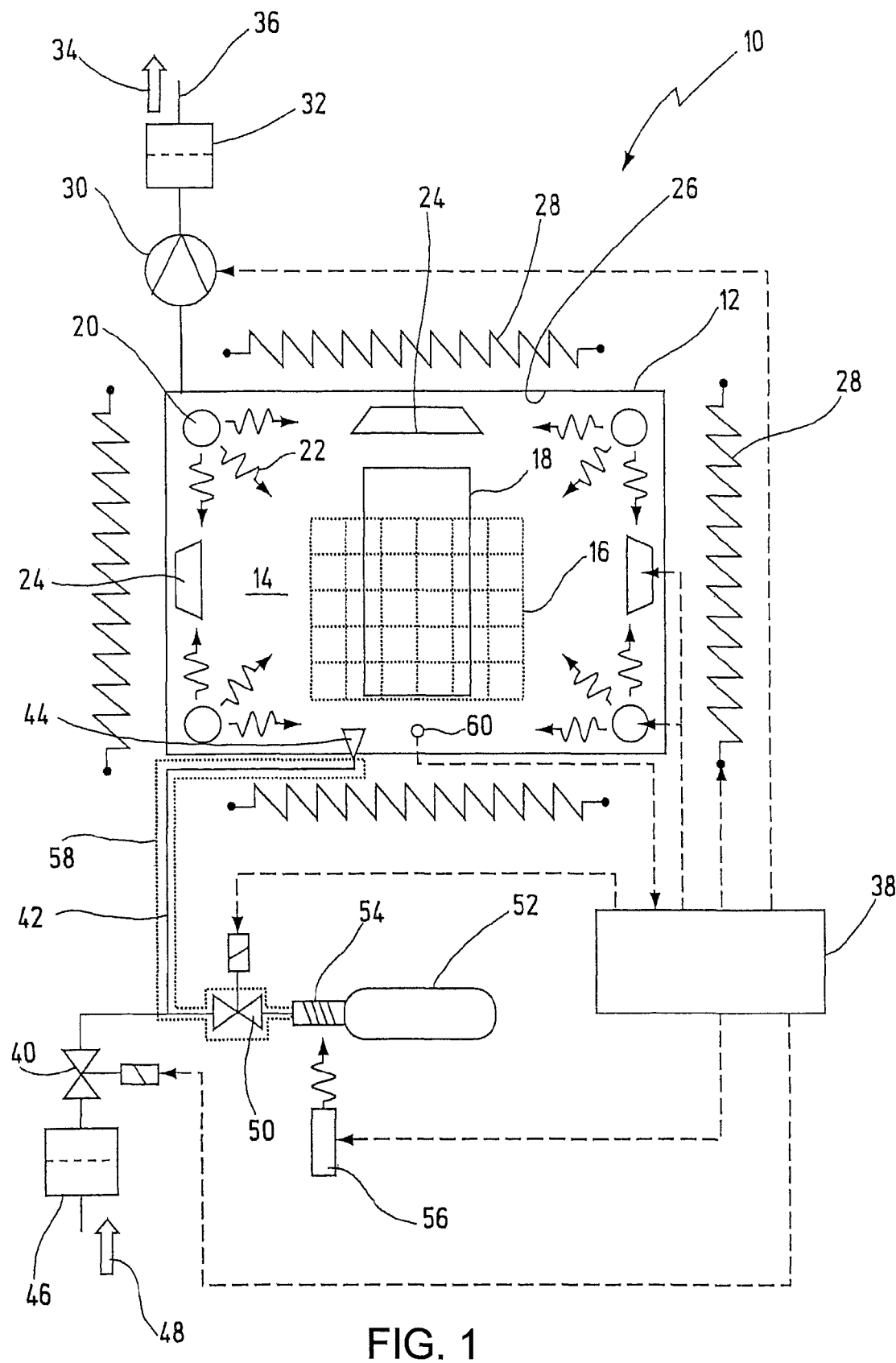
FIG. 1 illustrates an exemplary embodiment of the novel apparatus, in a schematic form, which is annotated by reference number 10 in its totality.

As shown in FIG. 1, the apparatus 10 comprises a vacuum chamber 12 with an internal space 14. In this case, a grating box 16 is shown in the internal space 14, in which an object 18 to be decontaminated is located. The grating box 16 makes it easy to feed the vacuum chamber 12, but it is not essential for implementation of the apparatus according to the invention.

Infrared radiators 20 are arranged in the internal space 14, each of which produces infrared radiation 22 (when required) for heating the object 14. By way of example, infrared radiators 20 are in this case illustrated at all four corners of the vacuum chamber 12. The object to be contaminated is thus, so to speak, surrounded by the infrared radiators 20, thus allowing particularly uniform and effective heating. As an alternative to this, in other embodiments of the invention, it is possible for infrared radiators to be arranged on both sides or only above the object 18 to be decontaminated.

In the present embodiment, reference number 24 denotes three UV radiators which can be used to irradiate the object to be contaminated with UV radiation for disinfection.

In this case, further heating means 28 are arranged along the inner walls 26 of the vacuum chamber 12. Preferably, each inner wall of the vacuum chamber 12 is heated (heating on all sides), thus effectively preventing the formation of condensation in the internal space 14 of the chamber 12. The heaters 28 are preferably in the form of electrical heaters. As an alternative to this, the internal walls 26 may, for example, be heated with hot air and/or hot gas, which are produced by a burner (preferably a diesel burner or multi-fuel burner). For this purpose, the inner walls may be provided with suitable channels (not illustrated here) for the hot air to be passed through.

Reference number 30 denotes a vacuum pump which can be used to evacuate the internal space 14 of the chamber 10. The vacuum pump is preferably a vane-type rotary pump. In a preferred embodiment, the vacuum pump 30 is designed such that the internal space of the chamber 10 can be evacuated to an internal pressure of about 1 Pa. On the downstream side, the vacuum pump 30 is connected to a filter. In one particularly preferred embodiment, this is a so-called HEPA filter (high-efficiency particle absorber), which is able to filter out even very small particles. It is also preferable for the filter 32 to be equipped with activated carbon (not illustrated here). The filter 32 is thus able to remove hazardous substances from the exhaust air 34 at the outlet 36, which hazardous substances have been released during vaporization of chemical substances in the vacuum chamber 10. Furthermore, the filter 32 is preferably designed to remove toxic decontamination agents, or any other hazardous decontamination agents, from the exhaust air 34, with such decontamination agents having been used for disinfection of an object 18.

Reference number 38 denotes a control unit which is used to control the process parameters in a defined manner. For this purpose, the control unit 38 is connected in particular to the infrared radiators 20, the UV radiators 24, the casing heater 28 and the vacuum pump 30. In other words, the last-mentioned elements are driven as required via the control unit 38. The control unit is designed to carry out the decontamination process using the temperature and the internal pressure in the chamber in a defined manner, and with defined process parameters.

Reference number 40 denotes a ventilation valve, which is set to be open or closed by means of the control unit 38. The ventilation valve 40 is connected via a supply line 42 to an inlet 44, which opens in the internal space 14 of the chamber 10. A second filter 46 is arranged upstream of the ventilation valve 40 and removes contamination from the incoming fresh air 48. This is preferably likewise an HEPA filter with activated carbon.

Reference number 50 denotes a second valve, which is set to be open or closed by means of the control unit 38. The valve 50 is used to fill the chamber 12 with a decontamination agent, for example hydrogen peroxide, formalin, peracetic acid or ethylene oxide. The first-mentioned decontamination agents are in this case preferred, because they are less toxic than ethylene oxide.

Reference number 52 denotes a reservoir which is used to provide the chemical decontamination agent. In the preferred embodiment, the apparatus 10 also comprises a vaporizer 54, which can be used to vaporize a liquid decontamination agent, for example peracetic acid or a formalin solution, from the reservoir 52 without any condensation. For this purpose, the vaporizer 54 comprises a heater 56, which is likewise driven by the control unit 38.

In this case, the output side of the gas-flow control valve 50 is connected to the supply line 42. As an alternative to this, the fresh-air supply and the supply of the decontamination agent could also be provided via completely separate supply lines into the vacuum chamber. In contrast, the present implementation has the advantage that the supply line for the decontamination agent is also purged virtually completely during the purging of the vacuum chamber.

In the preferred embodiment, the entire supply line path for filling of the vacuum chamber 10 with the decontamination agent can be heated. An appropriate casing heater is illustrated schematically by the reference number 58 in the FIGURE. The casing heater 58 may in this case also be in the form a heat conductor, which uses the output heat from the heater 56 to heat the supply line 42. It is preferred if the supply path for the decontamination agent can be heated completely, so that the formation of condensation from a vaporized decontamination agent is completely prevented.

Reference number 60 represents a pressure sensor which the control unit 38 can use to determine the internal pressure in the internal space 14 of the chamber 12. The pressure sensor 60 makes it possible to regulate the internal pressure at a desired value by means of the vacuum pump 30. Furthermore, the pressure sensor 60 is used in a preferred embodiment of the invention to set the concentration of decontamination agent in the internal space 14 of the chamber 12.

For detoxification of a contaminated object 18, the apparatus 10 is preferably operated as follows: the object 18 is inserted into the internal space 14 of the chamber 12, and the chamber 12 is closed such that it is pressuretight. The internal space 14 of the chamber 12 is then evacuated by means of the control unit 38 and the vacuum pump 30, preferably to an internal pressure of about 1 Pa (vacuum). The internal space 14 of the chamber 12 is heated at the same time that the vacuum is produced, or after the vacuum has been produced, preferably using the casing heater 28 and the infrared radiator 22. The internal space 14 is heated to about 70° C., which is detected by means of a temperature sensor not illustrated here.

The reduced pressure (vacuum) in the internal space 14 of the chamber 12 results in vaporization of any chemical contamination that is present, despite the comparatively low temperature. The internal space 14 is ventilated after allowing a certain amount of time to pass, that is to say fresh air 48 is fed into the internal space 14 via the ventilation valve 40. The internal space 14 is then evacuated, or it is evacuated at the same time, thus sucking out the vaporized contamination. The outlet air is cleaned by means of the filter 32. The entire process is preferably repeated a number of times, in order to ensure optimum detoxification of the object 18.

In contrast to the known detoxification methods, no hot vapor and no flue gas either is therefore required for decontamination in this case. The detoxification can be based only on the vaporization of chemical substances at relatively low temperatures as a result of the reduced pressure or vacuum.

For disinfection of an object, a chemical decontamination agent is fed into the internal space 14 via the gas-flow control valve 50 at the same time as or after the evacuation of the internal space 14. A chemical decontamination agent should for this purpose be understood as covering all substances which deactivate biological contamination as a result of not exclusively thermal interaction. In the preferred variant of the method, which also corresponds to the apparatus described here, the decontamination agent is fed in just by means of the reduced pressure in the chamber 12. In other words, the chemical decontamination agent is sucked into the chamber 12 because of the reduced pressure.

In addition to the use of the chemical decontamination agent, the object 18 to be decontaminated can also be irradiated by the UV radiators 24 in order to produce free radicals which interact with the substances to be decontaminated.

In preferred embodiments, hydrogen peroxide, formalin solution or peracetic acid is used a chemical decontamination agent. These agents are vaporized without any condensation before being introduced into the internal space 14 of the chamber 12. The concentration of the decontamination agent in the chamber 12 can be determined by means of the pressure sensor 60 in the preferred apparatus, and can be set in the desired manner via the control unit 38. All that is necessary for this purpose is to know the concentration of the decontamination agent in the aqueous solution in the reservoir 52. Furthermore, the internal pressure in the internal space 14 of the chamber 12 and the temperature in the chamber 12 are required before the decontamination agent is introduced. Since the internal pressure in the chamber increases while the gaseous decontamination agent is being fed in, the instantaneous concentration of the decontamination agent in the chamber 12 can be determined from the pressure difference. Dalton's ideal gas law is used for this purpose. The concentration is then given by:

$$\frac{n}{V} = \frac{\Delta p}{R \cdot T}$$

where
n is the amount of the substance,
V is the volume in the chamber,
Δp is the pressure difference between the pressure in the chamber before and after the introduction of the vaporized decontamination agent,
R is the gas constant, and
T is the temperature in the chamber.

However, as an alternative to this, it would basically be possible to provide suitable gas sensors for instrumentation detection of the respective decontamination agent concentration in the chamber 14. However, the preferred refinement is simpler, more cost-effective and more robust, and this is particularly advantageous for mobile use in military applications. It also produces statistical measurement inaccuracies which can occur because of the small number of molecules in the internal space when using gas sensors.

Since the determination of the concentration of the decontamination agent by means of the pressure difference between and after the decontamination agent is supplied is, on the other hand, inaccurate if the decontamination agent that is supplied in gaseous form condenses on its way to the chamber or in the chamber, the last-mentioned variant is in fact particularly advantageous if the formation of condensation is prevented by the inner walls 26 of the chamber 12 being heated on all sides, and by the heating of the supply line 42.

There is no need for exact pressure determination and the heating of the supply line path when using a decontamination agent, such as ethylene oxide, which is already in gaseous form from the start.

The advantage of the novel apparatus and of the novel method is in particular the simple, but reliable, setting of the atmospheric conditions in the internal space 14 of the chamber 12. The decontamination success can be guaranteed indirectly and in a simple manner by ensuring the process parameters, once they have been defined, without any need to carry out complex measurements or other types of analysis of the content of hazardous substances in the chamber and/or on the object to be decontaminated.

What is claimed is:

1. A method for removing biological contaminants from an object, comprising the steps of:
   providing a vacuum chamber having a plurality of inner walls surrounding an internal space,
   inserting the object into the internal space,
   evacuating the internal space by means of a vacuum pump to an internal pressure of less than 50 Pa,
   heating the object in the internal space by means of at least one heat radiator arranged in the internal space remote from the object, and heating the plurality of internal walls by means of a casing heater designed to heat all the internal walls,
   supplying a gaseous chemical decontamination agent into the internal space, and
   ventilating the internal space subsequently,
   wherein formation of condensation of the gaseous chemical decontamination agent in the internal space is prevented by use of the at least one heat radiator and the casing heater,
   wherein a pressure rise and a temperature in the internal space is determined while the internal space is being filled with the gaseous chemical decontamination agent, and
   wherein the concentration of the gaseous chemical decontamination agent in the internal space is controlled as a function of the pressure rise and the temperature in the internal space in accordance with Dalton's ideal gas law.

2. The method of claim 1, wherein a concentration of the decontamination agent in the internal space is determined using the pressure rise and temperature, and the decontamination agent is supplied to the internal space as a function of the decontamination agent concentration.

3. The method of claim 1, wherein the internal pressure in the internal space is constantly monitored in order to detect the pressure rise.

4. The method of claim 1, wherein the decontamination agent defines a saturation pressure, and the decontamination agent is supplied to the internal space such that the internal pressure is constantly kept below the saturation pressure.

5. The method of claim 1, wherein the internal space is evacuated to an internal pressure of less than 10 Pa.

6. The method of claim 1, wherein the internal space is evacuated to an internal pressure of about 1 Pa.

7. The method of claim 1, wherein the gaseous decontamination agent is vaporized from a liquid or solid form of the decontamination agent without any condensation.

8. The method of claim 1, wherein the gaseous decontamination agent is supplied to the internal space via a supply line, which is completely heated.

9. A method for removing biological contaminants from an object, comprising the steps of:
   providing a vacuum chamber having inner walls surrounding an internal space,
   inserting the object into the internal space,
   evacuating the internal space by means of a vacuum pump to an internal pressure of less than 50 Pa,
   heating the object in the internal space by means of at least one heat radiator arranged in the internal space and heating the internal walls by means of a casing heater,
   introducing a concentration of a gaseous chemical decontamination agent into the internal space, wherein formation of condensation of the gaseous chemical decontamination agent in the internal space is prevented by use of the at least one heat radiator and the casing heater,
   monitoring the pressure and temperature within said internal space, and
   controlling the concentration of gaseous chemical decontamination agent introduced into the internal space in accordance with said monitored pressure and temperature.

10. The method of claim 9, wherein the internal space is evacuated to an internal pressure of less than 10 Pa.

11. A method for removing biological contaminants from an object, comprising the steps of:
   providing a vacuum chamber having inner walls surrounding an internal space,
   inserting the object into the internal space, evacuating the internal space by means of a vacuum pump to an internal pressure of less than 50 Pa, introducing a gaseous chemical decontamination agent into the internal space, and heating the object in the internal space by means of at least one heat radiator arranged in the internal space, and heating the internal walls by means of a casing heater designed to heat all internal walls, thus preventing formation of condensation of the gaseous chemical decontamination agent in the internal space.

12. The method of claim 11, wherein the internal space is evacuated to an internal pressure of less than 10 Pa.

* * * * *